US012611488B2

(12) United States Patent
Huang et al.

(10) Patent No.: US 12,611,488 B2
(45) Date of Patent: Apr. 28, 2026

(54) PHOTOCURABLE COMPOSITE HYDROGEL MATRIX PRECURSOR, PREPARATION METHOD THEREOF AND SCAFFOLD WITH SAME

(71) Applicants: SHANDONG UNIVERSITY, Jinan (CN); YANSHAN UNIVERSITY, Qinhuangdao (CN)

(72) Inventors: Chuanzhen Huang, Qinhuangdao (CN); Xu Han, Jinan (CN); Hanlian Liu, Jinan (CN); Peng Yao, Jinan (CN); Hongtao Zhu, Jinan (CN); Bin Zou, Jinan (CN); Jun Wang, Jinan (CN)

(73) Assignees: SHANDONG UNIVERSITY, Jinan (CN); YANSHAN UNIVERSITY, Qinhuangdao (CN)

( * ) Notice: Subject to any disclaimer, the term of this patent is extended or adjusted under 35 U.S.C. 154(b) by 666 days.

(21) Appl. No.: 17/911,188

(22) PCT Filed: Sep. 17, 2021

(86) PCT No.: PCT/CN2021/119124
§ 371 (c)(1),
(2) Date: Sep. 13, 2022

(87) PCT Pub. No.: WO2023/024202
PCT Pub. Date: Mar. 2, 2023

(65) Prior Publication Data
US 2024/0216581 A1 Jul. 4, 2024

(30) Foreign Application Priority Data

Aug. 26, 2021 (CN) ......................... 202110988608.X

(51) Int. Cl.
| | |
|---|---|
| *A61L 27/52* | (2006.01) |
| *A61L 27/20* | (2006.01) |
| *A61L 27/22* | (2006.01) |
| *B33Y 10/00* | (2015.01) |
| *B33Y 80/00* | (2015.01) |
| *C08J 3/075* | (2006.01) |

(52) U.S. Cl.
CPC .............. *A61L 27/52* (2013.01); *A61L 27/20* (2013.01); *A61L 27/222* (2013.01); *B33Y 10/00* (2014.12); *B33Y 80/00* (2014.12); *C08J 3/075* (2013.01); *C08J 2305/04* (2013.01); *C08J 2401/28* (2013.01); *C08J 2405/00* (2013.01); *C08J 2405/08* (2013.01)

(58) Field of Classification Search
CPC ........ A61L 27/52; A61L 27/20; A61L 27/222; A61L 27/26; A61L 27/025; A61L 27/50; A61L 27/54; A61L 2300/236; B33Y 10/00; B33Y 80/00; B33Y 70/00; B33Y 70/10; C08J 3/075; C08J 2305/04; C08J 2401/28; C08J 2405/00; C08J 2405/08
See application file for complete search history.

(56) References Cited

U.S. PATENT DOCUMENTS

| | | |
|---|---|---|
| 2013/0172985 A1 | 7/2013 | Prestwich et al. |
| 2018/0117215 A1 | 5/2018 | Eslami et al. |

FOREIGN PATENT DOCUMENTS

| | | | |
|---|---|---|---|
| CN | 107744602 A | | 3/2018 |
| CN | 109942752 A | | 6/2019 |
| CN | 111574816 A | | 8/2020 |
| CN | 111729129 A | | 10/2020 |
| CN | 213130115 U | * | 5/2021 |
| CN | 112898599 A | | 6/2021 |
| CN | 113262325 A | | 8/2021 |
| CN | 113274554 A | | 8/2021 |
| CN | 113713179 A | | 11/2021 |
| WO | 2018/090189 A1 | | 5/2018 |
| WO | 2020/234167 A1 | | 11/2020 |

OTHER PUBLICATIONS

CN213130115U—machine translation (Chen et. al.), "Osteocartilage scaffold" May 7, 2021 Publication. (Year: 2021).*
Sun et al. "Synthesis and Properties of Gelatin Methacryloyl (GelMA) Hydrogels and Their Recent Applications in Load-Bearing Tissue" Polymers, Oct. 2018, 1290. (Year: 2018).*
CN213130115U—machine translation. Chen et. al. "Osteocartilage scaffold" (Year: 2021).*
Levett et. al. "A biomimetic extracellular matrix for cartilage tissue engineering centered on photocurable gelatin, hyaluronic acid and chondroitin sulfate" Acta Biomaterialia 10 (2014) 214-223. (Year: 2014).*

(Continued)

*Primary Examiner* — Sean M Basquill
*Assistant Examiner* — Rajan Pragani
(74) *Attorney, Agent, or Firm* — IPro, PLLC; Na Xu

(57) ABSTRACT

A photocurable composite hydrogel matrix precursor, a preparation method thereof and a scaffold with same. The photocurable composite hydrogel matrix precursor includes gelatin methacrylate, sodium alginate, sodium carboxymethyl cellulose and chondroitin sulfate, where the mass ratio of a photoinitiator to the gelatin methacrylate to the sodium alginate to the sodium carboxymethyl cellulose to the chondroitin sulfate is (0.2-0.3):(8-10):(1-3):(0.6-0.8):(0.05-0.07). By adoption of the precursor, a cell-loaded printing hydrogel scaffold can be obtained through an extrusion-based 3D bio-printing technology, and the scaffold is controllable in form, good in moldability, high in precision, and has good stability; the biocompatibility and bioactivity are high, so that a good growing environment can be provided for fibroblasts; and the preparation process is simple and can be completed within a short time, moreover, the porosity and mechanical performance of the 3D printing hydrogel scaffold can be adjusted by adjusting the raw material ratio.

5 Claims, 3 Drawing Sheets

(56) References Cited

OTHER PUBLICATIONS

Buhus et. al. "Controlled Release of Water Soluble Antibiotics By Carboxymethylcellulose- and Gelatin-Based Hydrogels Cross-linked With Epichlorohydrin" Cellulose Chem. Technol., 43 (4-6), 141-151 (2009) (Year: 2009).*

CN213130115U, machine translation provided. Chen "Osteocartilage scaffold" May 7, 2021 (Year: 2021).*

Buhus Controlled Release of Water Soluble Antibiotics by Carboxymethylcellulose- and Gelatin-Based Hydrogels Cross-linked With Epichlorohydrin Cellulose Chem. Technol., 43 (4-6), 141-151 (2009) (Year: 2009).*

Levett "A biomimetic extracellular matrix for cartilage tissue engineering centered on photocurable gelatin, hyaluronic acid and chondroitin sulfate" Acta Biomaterialia 10 (2014) 214-223 (Year: 2014).*

May 27, 2022 International Search Report issued in International Patent Application No. PCT/CN2021/119124.

May 27, 2022 Written Opinion issued in International Patent Application No. PCT/CN2021/119124.

Mar. 17, 2022 Office Action issued in Chinese Patent Application No. 202110988608.X.

Hadi Rastin et al. "3D Bioprinting of Methylcellulose/Gelatin-Methacryloyl (MC/GELMA) Bioink With High Shape Integrity". ACS Applied Bio Materials, 2020, vol. 3, issue 3, pp. 1815-1826.

Marco Costantini et al. "3D Bioprinting of BM-MSCs-Loaded ECM Biomimetic Hydrogels for in Vitro Neocartilage Formation". International Society for Biofabrication, 2016, vol. 8, issue 3, pp. 035002.

Shuai Li et al. "Fabrication of Thermoresponsive Hydrogel Scaffolds With Engineered Microscale Vasculatures". Advanced Functional Materials, 2021, vol. 31, issue 27, pp. 2102685.

Jin Liu et al. "Fabrication of 3D-Printed Fish-Gelatin-Based Polymer Hydrogel Patches for Local Delivery of Pegylated Liposomal Doxorubicin". Marine Drugs, 2020, vol. 18, issue 6, pp. 325.

Henry H. Hwang et al. "3D-Printing of Functional Biomedical Microdevices Via Light- and Extrusion-Based Approaches". Small Methods, 2017, vol. 2, issue 2, pp. 1700277.

Chen Haiting. "3D Printing of SA/GELMA Hydrogel Scaffold for Bone Repair Applications". South China University of Technology, Chinese Master's Theses Full-Text Database of Medical and Health Technology, issue 12, 2018.

Anne Metje Van Genderen et al. "Microfluidic Bioprinting for Engineering Vascularized Tissues and Organoids". Journal of Visualized Experiments, 2017, vol. 126.

Eva Hoch et al. "Biopolymer-Based Hydrogels for Cartilage Tissue Engineering". Bioinspired, Biomimetic, and Nanobiomaterials, vol. 5, issue 2, pp. 51-66, 2016.

Yanfei Xi. "Introduction to Marine Biomedical Materials", Shanghai Scientific & Technical Publishers.

* cited by examiner

PHOTOCURABLE COMPOSITE HYDROGEL MATRIX PRECURSOR, PREPARATION METHOD THEREOF AND SCAFFOLD WITH SAME

TECHNICAL FIELD

The present invention relates to the technical field of medical materials, and particularly relates to a photocurable composite hydrogel matrix precursor, a preparation method thereof and a scaffold with same.

BACKGROUND

Information of the Related Art part is merely disclosed to increase the understanding of the overall background of the present invention, but is not necessarily regarded as acknowledging or suggesting, in any form, that the information constitutes the prior art known to a person of ordinary skill in the art.

With the advancement of medical means, organ transplantation and repair technology have been greatly developed, and organ transplantation has become a main treatment means for end-stage organ diseases. However, there is an extreme shortage of donor organs at present, consequently, organ transplantation is limited. In addition, a traditional bionic scaffold has no physiological activity and has many defects. An assumption of "cell printing" is put forward based on the biological self-assembly principle. Through the cell printing technology, cells, growth factors and scaffolds can be combined into a complete overall structure which can perform normal biological functions, and therefore cell-loaded 3D bio-printing is developed as the occasion demands.

Traditional biomaterial manufacturing and synthesis strategies include molding, blending, microfluidic technology, magnetic assembly technology and the like. In contrast, the 3D bio-printing technology can be used for manufacturing more accurate tissue structures and tissue models with controllable porous structures in a high-throughput manner, and it greatly reduces the treatment time during tissue and organ transplantation compared with a traditional organ transplantation solution. In addition, this technology allows local culture of living cells of various types and customizable patterning customization of various biological products, and promotes designated delivery of drugs, genes and growth factors, integration of vascularization in biological tissues in tissue engineering, etc. Therefore, the biomaterial should have appropriate physical and chemical properties, good biocompatibility, and printability under shear thinning to reduce extrusion damage to cells in the printing process while ensuring sufficient mechanical properties, and also should have the characteristics of being suitable for cell adhesion, migration, proliferation and providing a specific microenvironment and the like. Therefore, it is still difficult to prepare a hydrogel material with a good comprehensive performance for 3D bio-printing.

SUMMARY

In order to solve the problems in the prior art, an objective of the present invention is to provide a photocurable composite hydrogel matrix precursor, a preparation method thereof and a scaffold with same. The photocurable composite hydrogel matrix precursor can be used for extrusion-based 3D bio-printing. The prepared photocurable composite hydrogel of the present invention has the advantages of being good in biocompatibility, low in toxicity, adjustable in mechanical performance, complete in moldability under the dual properties of extrudability and photocuring, and capable of providing a three-dimensional living environment for cells, and is a 3D bio-printing composite hydrogel material capable of promoting adhesion and proliferation of cells on a three-dimensional scaffold.

To achieve the foregoing objective of the present invention, the present invention provides the following technical solutions:

In the first aspect, the present invention provides a photocurable composite hydrogel matrix precursor, including the following components:

a photoinitiator;

gelatin methacrylate;

sodium alginate;

sodium carboxymethyl cellulose; and chondroitin sulfate;

where the mass ratio of the photoinitiator to the gelatin methacrylate to the sodium alginate to the sodium carboxymethyl cellulose to the chondroitin sulfate is (0.2-0.3):(8-10):(1-3):(0.6-0.8):(0.05-0.07).

In the second aspect, the present invention provides a method for preparing the photocurable composite hydrogel matrix precursor, including:

(1) dissolving the photoinitiator in a PBS solution to form a photoinitiator solution;

(2) preparing a mixed solution: respectively dissolving the gelatin methacrylate, the sodium alginate and the sodium carboxymethyl cellulose in the photoinitiator solution obtained in step (1) to correspondingly form a gelatin methacrylate solution, a sodium alginate solution and a sodium carboxymethyl cellulose solution, and mixing the solutions according to a certain volume proportion to obtain the mixed solution; and (3) preparing a composite solution: adding the chondroitin sulfate into the mixed solution obtained in step (2), performing stirring and dissolving to obtain the composite solution, i.e., the photocurable composite hydrogel matrix precursor.

In the third aspect, the present invention provides an extrusion-based 3D bio-printing composite hydrogel scaffold, being prepared by a method including:

(1) preparing a photocurable composite hydrogel matrix precursor according to the method for preparing the photocurable composite hydrogel matrix precursor described in the second aspect; and (2) performing extrusion 3D printing on the matrix precursor prepared in step (1) to obtain the hydrogel scaffold: uniformly mixing the matrix precursor and mouse fibroblasts, and performing extrusion printing through a 3D bio-printer to form a scaffold; and soaking the scaffold with a calcium chloride solution to enable ion crosslinking, then performing ultraviolet irradiation to realize photo-crosslinking to obtain the extrusion-based 3D bio-printing composite hydrogel scaffold.

The implementations of the present invention have the following beneficial effects:

(1) the cell-loaded printing hydrogel scaffold can be achieved by an extrusion-based 3D bio-printing technology, and the scaffold is controllable in form, good in moldability and high in precision, and has good stability;

(2) the added gelatin methacrylate, sodium alginate, sodium carboxymethyl cellulose and chondroitin sulfate materials have good biocompatibility and bioactivity and can provide a good growing environment for fibroblasts, which further indicates the feasibility of hydrogel applied to tissue engineering; and (3) the preparation process is simple and can be completed in a short time, moreover, the reaction requirement is simple, and the porosity and mechanical performance of the 3D printing hydrogel scaffold can be adjusted by adjusting the proportion of the gelatin methacrylate and the sodium carboxymethyl cellulose in a hydrogel system.

BRIEF DESCRIPTION OF THE DRAWINGS

The accompanying drawings constituting a part of the present invention are used to provide a further understanding of the present invention. The exemplary examples of the present invention and descriptions thereof are used to explain the present invention, and do not constitute an improper limitation of the present invention.

DETAILED DESCRIPTION

Figure 1:
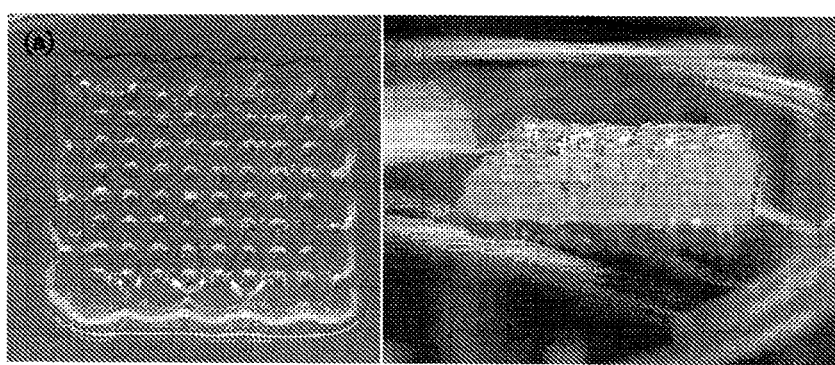
FIG. 1 is a diagram of an extrusion 3D printing scaffold in an Example 3 of the present invention.
Figure 1:
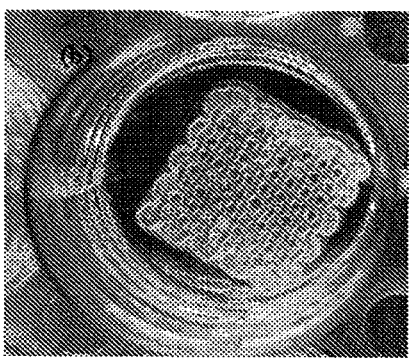

It should be pointed out that the following detailed descriptions are all illustrative and are intended to provide further descriptions of the present invention. Unless otherwise specified, all technical and scientific terms used herein have the same meanings as those usually understood by a person of ordinary skill in the art to which the present invention belongs.

It should be noted that terms used herein are only for describing specific implementations and are not intended to limit exemplary implementations according to the present invention. As used herein, the singular form is also intended to include the plural form unless the context clearly dictates otherwise. In addition, it should further be understood that, terms "comprise" and/or "include" used in this specification indicate that there are features, steps, operations, devices, components, and/or combinations thereof.

In an embodiment of the present invention, provided is a photocurable composite hydrogel matrix precursor, including:

a photoinitiator;
gelatin methacrylate;
sodium alginate;
sodium carboxymethyl cellulose; and
chondroitin sulfate;
where the mass ratio of the photoinitiator to the gelatin methacrylate to the sodium alginate to the sodium carboxymethyl cellulose to the chondroitin sulfate is (0.2-0.3):(8-10):(1-3):(0.6-0.8):(0.05-0.07), preferably 0.25:10:2:0.7:0.06.

In some embodiments of the present invention, lithium phenyl-2,4,6-trimethylbenzoyl phosphinate (LAP) is selected as the photoinitiator.

Gelatin methacrylate (GelMA) has extrudable printing capacity, temperature sensitivity and photocuring performance, also has good biocompatibility and good biodegradability and can adjust cell adhesion; sodium alginate (Alg) can keep high resolution, is good in biodegradability and has the characteristic of maintaining a wound healing environment; sodium carboxymethyl cellulose (NaCMC) is one of natural high polymer materials and can increase viscosity and mechanical performance while guaranteeing biocompatibility; and chondroitin sulfate (CS) is a kind of glycosaminoglycan covalently linked to protein to form proteoglycan, and chondroitin sulfate is widely distributed on extracellular matrixes and cell surfaces of animal tissue and has the effects of diminishing inflammation and sterilizing.

According to the photocurable composite hydrogel of the present invention, under the presence of free radicals generated by the photoinitiator, the free radicals and a gelatin methacrylate GelMA monomer undergo a chain type growth reaction, in other words, covalent bonds are formed between gelatin methacrylate molecules to generate a polymerization network, and therefore the gelatin methacrylate molecules have good moldability; by soaking in a calcium chloride solution, sodium alginate in the hydrogel scaffold and calcium ions undergo ion crosslinking to further implement photocurable; and hydroxyl, carboxyl and ester radicals in carboxymethyl cellulose and chondroitin sulfate in the scaffold can form hydrogen bonds, which helps the network in the scaffold to be in a dynamic stable state, and therefore the structural stability of the scaffold is improved.

In the composite hydrogel of the present invention, the content of sodium carboxymethyl cellulose affects the performance of the finally-formed composite hydrogel, the stress changes faster along with strain as the content of sodium carboxymethyl cellulose increases, and the breaking strain value of the hydrogel is smaller; the higher the sodium carboxymethyl cellulose content is within a certain range, the stronger the hydrogel network is, which leads to the enhancement of the mechanical strength, and the larger the compression modulus of the hydrogel is; and in addition, the composite hydrogel is free of toxicity to cells, can promote cell proliferation to a certain degree, and has good biocompatibility.

In an embodiment of the present invention, provided is a method for preparing the photocurable composite hydrogel matrix precursor, including:

(1) dissolving the photoinitiator in a PBS solution to form a photoinitiator solution;

(2) preparing a mixed solution: respectively dissolving the gelatin methacrylate, the sodium alginate and the sodium carboxymethyl cellulose in the photoinitiator solution obtained in step (1) to correspondingly form a gelatin methacrylate solution, a sodium alginate solution and a sodium carboxymethyl cellulose solution, and mixing the solutions according to a certain volume proportion to obtain the mixed solution; and (3) preparing a composite solution: adding the chondroitin sulfate into the mixed solution obtained in step (2), performing stirring and dissolving to obtain the composite solution, i.e., the photocurable composite hydrogel matrix precursor.

In some embodiments of the present invention, in step (1), the photoinitiator is dissolved in the PBS solution and continuously heated in a water bath to 60-65° C. for 30-35 min.

In some embodiments of the present invention, in step (2), the dissolving is carried out under a condition of continuously heating in the water bath at 60-65° C.

In some embodiments of the present invention, in step (2), the volume fraction of the gelatin methacrylate solution in the mixed solution is 40-44%, preferably 42% (v/v).

In some embodiments of the present invention, in step (2), the volume fraction of the sodium alginate solution in the mixed solution is 14-18%, preferably 16% (v/v).

In some embodiments of the present invention, in step (2), the volume fraction of the sodium carboxymethyl cellulose solution in the mixed solution is 40-44%, preferably 42% (v/v).

In some embodiments of the present invention, in step (3), chondroitin sulfate is added, stirred and dissolved, and then a 0.22 μm sterile filter is used for filtering and sterilizing.

In some embodiments of the present invention, the solubility of the gelatin methacrylate solution in the composite solution is 10% (w/v); the concentration of the sodium alginate solution in the composite solution is 2% (w/v); the mass ratio of gelatin methacrylate to sodium carboxymethyl cellulose in the composite solution is 100:7; and the concentration of chondroitin sulfate in the composite solution is 0.006% (w/v).

In an embodiment of the present invention, provided is an extrusion-based 3D bio-printing composite hydrogel scaffold, being prepared by a method including:

(1) preparing a photocurable composite hydrogel matrix precursor according to the method for preparing the photocurable composite hydrogel matrix precursor described in the second aspect; and (2) performing extrusion 3D printing on the matrix precursor prepared in step (1) to obtain the hydrogel scaffold: uniformly mixing the matrix precursor and mouse fibroblasts, and performing extrusion printing through a 3D bio-printer to form a scaffold; and soaking the scaffold with a calcium chloride solution to enable ion crosslinking, then performing ultraviolet irradiation to realize photo-crosslinking to obtain the extrusion-based 3D bio-printing composite hydrogel scaffold.

In some embodiments of the present invention, in step (2), the printing speed is 380-400 mm/min, the moving speed is 850-900 mm/min, the layer height is 0.25 mm, the number of layers is 3, the distance is 1.5 mm*1.5 mm, the length*width is 12 mm*12 mm, the boundary length is 1 mm, the boundary printing speed is 300 mm/min, the nozzle model is 25 G, the nozzle temperature is 23° C., the receiving platform temperature is 5° C., and the precision air pressure is 27.4 KPa.

In some embodiments of the present invention, step (2) is carried out in a sterile environment.

In some embodiments of the present invention, the mass fraction of the calcium chloride solution in step (2) is 4%; and the wavelength of ultraviolet light is 405 nm.

In some embodiments of the present invention, in step (2), the dosage ratio of the composite solution to mouse fibroblasts is 1 mL: $1 \times 10^6$-$1.5 \times 10^6$ pcs.

In the present invention, under the irradiation of ultraviolet light with a wavelength of 405 nm, the photoinitiator absorbs light energy to generate free radicals, the free radicals and the gelatin methacrylate monomer undergo the chain type growth reaction, in other words, covalent bonds are formed between the gelatin methacrylate molecules to generate the polymerization network, and therefore the gelatin methacrylate molecules have good moldability; by soaking in the calcium chloride solution, sodium alginate in the hydrogel scaffold and calcium ions undergo ion crosslinking to further implement photocurable; and hydroxyl, carboxyl and ester radicals in carboxymethyl cellulose and chondroitin sulfate in the scaffold can form hydrogen bonds, which helps network in the scaffold to be in the dynamic stability state, and therefore the structural stability of the scaffold is improved.

The present invention is further described below with reference to specific embodiments.

Example 1

(1) Preparation of an LAP solution: 0.1 g of a photoinitiator lithium phenyl-2,4,6-trimethylbenzoyl phosphinate (LAP) was dissolved in 40 ml of a PBS solution, the solution was continuously heated in a water bath to 60° C. for 30 min, oscillation was carried out 3 times during heating, and finally the LAP solution was obtained, with a concentration of 0.25% (w/v).

(2) Preparation of a mixed solution: a gelatin methacrylate (GelMA) solution, a sodium alginate (Alg) solution and a sodium carboxymethyl cellulose (NaCMC) solution were prepared respectively, specifically, 1 g of gelatin methacrylate was dissolved in 10 ml of a PBS solution, namely, the solubility of the gelatin methacrylate solution was 10% (w/v); 0.2 g of sodium alginate was dissolved in 10 ml of the PBS solution, namely, the concentration of the sodium alginate solution was 2% (w/v); sodium carboxymethyl cellulose was not dissolved in 10 ml of the PBS solution, namely, the mass ratio of the gelatin methacrylate (GelMA) to the sodium carboxymethyl cellulose (NaCMC) was 100:0; all the above solutions were respectively continuously heated in the water bath at 60° C., oscillation was carried out 3 times during heating until the solutions were completely dissolved. Then 4.2 ml of the gelatin methacrylate solution, 1.6 ml of the sodium alginate solution and 4.2 ml of the sodium carboxymethyl cellulose solution were respectively taken and placed in a container and stirred uniformly, and during stirring, the solutions were continuously heated in the water bath at 60° C., and oscillation was carried out 3 times, thereby obtaining 10 ml of the mixed solution.

(3) Preparation of a composite solution: 0.006 g of chondroitin sulfate (CS) was added into 10 mL of the mixed solution, and stirred and dissolved, a 0.22 μm sterile filter was used for filtering and sterilizing, and finally the composite solution was obtained.

(4) Preparation of a hydrogel scaffold through the prepared composite solution by extrusion-based 3D printing: the composite solution and mouse fibroblasts were uniformly mixed in a sterile environment, where the dosage ratio of the composite solution to the mouse fibroblasts was 1 mL: $1 \times 10^6$ pcs; and a 3D bio-printer was used for conducting extrusion printing to form the scaffold, where the printing parameters were that the printing speed was 400 mm/min, the moving speed was 900 mm/min, the layer height was 0.25 mm, the number of layers was 3, the distance was 1.5 mm*1.5 mm, the length*width was 12 mm*12 mm, the boundary length was 1 mm, the boundary printing speed was 300 mm/min, the nozzle model was 25 G, the nozzle temperature was 23° C., the receiving platform temperature was 5° C., and the precision air pressure was 27.4 KPa.

Finally, the hydrogel scaffold was soaked with a 4% sterile calcium chloride solution for 3 min to enable ion crosslinking, then the hydrogel scaffold was irradiated through 405 nm ultraviolet light to realize photo-crosslinking to obtain the extrusion-based 3D bio-printing composite hydrogel scaffold.

Example 2

(1) Preparation of an LAP solution: 0.1 g of a photoinitiator lithium phenyl-2,4,6-trimethylbenzoyl phosphinate (LAP) was dissolved in 40 ml of a PBS solution, the solution was continuously heated in a water bath to 60° C. for 30 min, oscillation was carried out 3 times during heating, and finally the LAP solution was obtained, with a concentration of 0.25% (w/v).

(2) Preparation of a mixed solution: a gelatin methacrylate solution, a sodium alginate solution and a sodium carboxymethyl cellulose solution were prepared respectively, specifically, 1 g of gelatin methacrylate was dissolved in 10 ml of a PBS solution, namely, the solubility of the gelatin methacrylate solution was 10% (w/v); 0.2 g of sodium alginate was dissolved in 10 ml of the PBS solution, namely, the concentration of the sodium alginate solution was 2% (w/v); 0.04 g of sodium carboxymethyl cellulose was dissolved in 10 ml of the PBS solution, namely, the mass ratio of the gelatin methacrylate (GelMA) to the sodium carboxymethyl cellulose (NaCMC) was 100:4; all the above solutions were respectively continuously heated in the water bath at 60° C., oscillation was carried out 3 times during heating until the solutions were completely dissolved. Then 4.2 ml of the gelatin methacrylate solution, 1.6 ml of the sodium alginate solution and 4.2 ml of the sodium carboxymethyl cellulose solution were respectively taken and placed in a container and stirred uniformly, and during stirring, the solutions were continuously heated in the water bath at 60° C., and oscillation was carried out 3 times, thereby obtaining 10 ml of the mixed solution.

(3) Preparation of a composite solution: 0.006 g of chondroitin sulfate was added into 10 mL of the mixed solution, and stirred and dissolved, a 0.22 μm sterile filter was used for filtering and sterilizing, and finally the composite solution was obtained.

(4) Preparation of a hydrogel scaffold through the prepared composite solution by extrusion-based 3D printing: the composite solution and mouse fibroblasts were uniformly mixed in a sterile environment, where the dosage ratio of the composite solution to the mouse fibroblasts was 1 mL: $1 \times 10^6$ pcs; and a 3D bio-printer was used for conducting extrusion printing to form the scaffold, where the printing parameters were that the printing speed was 400 mm/min, the moving speed was 900 mm/min, the layer height was 0.25 mm, the number of layers was 3, the distance was 1.5 mm*1.5 mm, the length*width was 12 mm*12 mm, the boundary length was 1 mm, the boundary printing speed was 300 mm/min, the nozzle model was 25 G, the nozzle temperature was 23° ° C., the receiving platform temperature was 5° C., and the precision air pressure was 27.4 KPa.

Finally, the hydrogel scaffold was soaked with a 4% sterile calcium chloride solution for 3 min to enable ion crosslinking, then the hydrogel scaffold was irradiated through 405 nm ultraviolet light to realize photo-crosslinking to obtain the extrusion-based 3D bio-printing composite hydrogel scaffold.

Example 3

(1) Preparation of an LAP solution: 0.1 g of a photoinitiator lithium phenyl-2,4,6-trimethylbenzoyl phosphinate (LAP) was dissolved in 40 ml of a PBS solution, the solution was continuously heated in a water bath to 60° C. for 30 min, oscillation was carried out 3 times during heating, and finally the LAP solution was obtained, with a concentration of 0.25% (w/v).

(2) Preparation of a mixed solution: a gelatin methacrylate solution, a sodium alginate solution and a sodium carboxymethyl cellulose solution were prepared respectively, specifically, 1 g of gelatin methacrylate was dissolved in 10 ml of a PBS solution, namely, the solubility of the gelatin methacrylate solution was 10% (w/v); 0.2 g of sodium alginate was dissolved in 10 ml of the PBS solution, namely, the concentration of the sodium alginate solution was 2% (w/v); 0.07 g of sodium carboxymethyl cellulose was dissolved in 10 ml of the PBS solution, namely, the mass ratio of the gelatin methacrylate (GelMA) to the sodium carboxymethyl cellulose (NaCMC) was 100:7; all the above solutions were respectively continuously heated in the water bath at 60° C., oscillation was carried out 3 times during heating until the solutions were completely dissolved. Then 4.2 ml of the gelatin methacrylate solution, 1.6 ml of the sodium alginate solution and 4.2 ml of the sodium carboxymethyl cellulose solution were respectively taken and placed in a container and stirred uniformly, and during stirring, the solutions were continuously heated in the water bath at 60° C., and oscillation was carried out 3 times, thereby obtaining 10 ml of the mixed solution.

(3) Preparation of a composite solution: 0.006 g of chondroitin sulfate was added into 10 mL of the mixed solution, and stirred and dissolved, a 0.22 μm sterile filter was used for filtering and sterilizing, and finally the composite solution was obtained.

(4) Preparation of a hydrogel scaffold through the prepared composite solution by extrusion-based 3D printing: the composite solution and mouse fibroblasts were uniformly mixed in a sterile environment, where the dosage ratio of the composite solution to the mouse fibroblasts was 1 mL: $1 \times 10^6$ pcs; and a 3D bio-printer was used for conducting extrusion printing to form the scaffold, where the printing parameters were that the printing speed was 400 mm/min, the moving speed was 900 mm/min, the layer height was 0.25 mm, the number of layers was 3, the distance was 1.5 mm*1.5 mm, the length*width was 12 mm*12 mm, the boundary length was 1 mm, the boundary printing speed was 300 mm/min, the nozzle model was 25 G, the nozzle temperature was 23° C., the receiving platform temperature was 5° C., and the precision air pressure was 27.4 KPa.

Finally, the hydrogel scaffold was soaked with a 4% sterile calcium chloride solution for 3 min to enable ion crosslinking, then the hydrogel scaffold was irradiated through 405 nm ultraviolet light to realize photo-crosslinking to obtain the extrusion-based 3D bio-printing composite hydrogel scaffold.

Example 4

(1) Preparation of an LAP solution: 0.1 g of a photoinitiator lithium phenyl-2,4,6-trimethylbenzoyl phosphinate (LAP) was dissolved in 40 ml of a PBS solution, the solution was continuously heated in a water bath to 60° C. for 30 min, oscillation was carried out 3 times during heating, and finally the LAP solution was obtained, with a concentration of 0.25% (w/v).

(2) Preparation of a mixed solution: a gelatin methacrylate solution, a sodium alginate solution and a sodium carboxymethyl cellulose solution were prepared respectively, specifically, 1 g of gelatin methacrylate was dissolved in 10 ml of a PBS solution, namely, the solubility of the gelatin methacrylate solution was 10% (w/v); 0.2 g of sodium alginate was dissolved in 10 ml of the PBS solution, namely, the concentration of the sodium alginate solution was 2% (w/v); 0.1 g of sodium carboxymethyl cellulose was dissolved in 10 ml of the PBS solution, namely, the mass ratio of the gelatin methacrylate (GelMA) to the sodium carboxymethyl cellulose (NaCMC) was 10:1; all the above solutions were respectively continuously heated in the water bath at 60° C., oscillation was carried out 3 times during heating until the solutions were completely dissolved. Then 4.2 ml of the gelatin methacrylate solution, 1.6 ml of the sodium alginate solution and 4.2 ml of the sodium carboxymethyl cellulose solution were respectively taken and placed in a container and stirred uniformly, and during stirring, the solutions were continuously heated in the water bath at 60° C., and oscillation was carried out 3 times, thereby obtaining 10 ml of the mixed solution.

(3) Preparation of a composite solution: 0.006 g of chondroitin sulfate was added into 10 mL of the mixed solution, and stirred and dissolved, a 0.22 μm sterile filter was used for filtering and sterilizing, and finally the composite solution was obtained.

(4) Preparation of a hydrogel scaffold through the prepared composite solution by extrusion-based 3D printing: the composite solution and mouse fibroblasts were uniformly mixed in a sterile environment, where the dosage ratio of the composite solution to the mouse fibroblasts was 1 mL: $1\times10^6$ pcs; and a 3D bio-printer was used for conducting extrusion printing to form the scaffold, where the printing parameters were that the printing speed was 400 mm/min, the moving speed was 900 mm/min, the layer height was 0.25 mm, the number of layers was 3, the distance was 1.5 mm*1.5 mm, the length*width was 12 mm*12 mm, the boundary length was 1 mm, the boundary printing speed was 300 mm/min, the nozzle model was 25 G, the nozzle temperature was 23° C., the receiving platform temperature was 5° C., and the precision air pressure was 27.4 KPa.

Finally, the hydrogel scaffold was soaked with a 4% sterile calcium chloride solution for 3 min to enable ion crosslinking, then the hydrogel scaffold was irradiated through 405 nm ultraviolet light to realize photo-crosslinking to obtain the extrusion-based 3D bio-printing composite hydrogel scaffold.

Example 5

(1) Preparation of an LAP solution: 0.1 g of a photoinitiator lithium phenyl-2,4,6-trimethylbenzoyl phosphinate (LAP) was dissolved in 40 ml of a PBS solution, the solution was continuously heated in a water bath to 60° C. for 30 min, oscillation was carried out 3 times during heating, and finally the LAP solution was obtained, with a concentration of 0.25% (w/v).

(2) Preparation of a mixed solution: a gelatin methacrylate solution, a sodium alginate solution and a sodium carboxymethyl cellulose solution were prepared respectively, specifically, 1 g of gelatin methacrylate was dissolved in 10 ml of a PBS solution, namely, the solubility of the gelatin methacrylate solution was 10% (w/v); 0.2 g of sodium alginate was dissolved in 10 ml of the PBS solution, namely, the concentration of the sodium alginate solution was 2% (w/v); 0.3 g of sodium carboxymethyl cellulose was dissolved in 10 ml of the PBS solution, namely, the mass ratio of the gelatin methacrylate (GelMA) to the sodium carboxymethyl cellulose (NaCMC) was 10:3; all the above solutions were respectively continuously heated in the water bath at 60° C., oscillation was carried out 3 times during heating until the solutions were completely dissolved. Then 4.2 ml of the gelatin methacrylate solution, 1.6 ml of the sodium alginate solution and 4.2 ml of the sodium carboxymethyl cellulose solution were respectively taken and placed in a container and stirred uniformly, and during stirring, the solutions were continuously heated in the water bath at 60° C., and oscillation was carried out 3 times, thereby obtaining 10 ml of the mixed solution.

(3) Preparation of a composite solution: 0.006 g of chondroitin sulfate was added into 10 mL of the mixed solution, and stirred and dissolved, a 0.22 μm sterile filter was used for filtering and sterilizing, and finally the composite solution was obtained.

(4) Preparation of a hydrogel scaffold through the prepared composite solution by extrusion-based 3D printing: the composite solution and mouse fibroblasts were uniformly mixed in a sterile environment, where the dosage ratio of the composite solution to the mouse fibroblasts was 1 mL: $1\times10^6$ pcs; and a 3D bio-printer was used for conducting extrusion printing to form the scaffold, where the printing parameters were that the printing speed was 400 mm/min, the moving speed was 900 mm/min, the layer height was 0.25 mm, the number of layers was 3, the distance was 1.5 mm*1.5 mm, the length*width was 12 mm*12 mm, the boundary length was 1 mm, the boundary printing speed was 300 mm/min, the nozzle model was 25 G, the nozzle temperature was 23° C., the receiving platform temperature was 5° C., and the precision air pressure was 27.4 KPa.

Finally, the hydrogel scaffold was soaked with a 4% sterile calcium chloride solution for 3 min to enable ion crosslinking, then the hydrogel scaffold was irradiated through 405 nm ultraviolet light to realize photo-crosslinking to obtain the extrusion-based 3D bio-printing composite hydrogel scaffold.

The following tests show the advantages of the hydrogel material of the examples of the present invention applied to tissue engineering scaffolds or cell-loaded printing tissue.

Moldability characterization: FIG. 1 shows 3D printing of a 3-layer porous scaffold through the hydrogel material in the Example 3, where FIG. 1 (a) shows a printed hydrogel scaffold that has been cross-linked just after printing, which can show a porous form and is free of swelling and collapse, and FIG. 1 (b) shows a hydrogel scaffold which has been soaked in the PBS solution for 5 days, inner pores of the hydrogel scaffold basically remain the original form, and are free of blockage and collapse, and the structure is stable.

Figure 2:
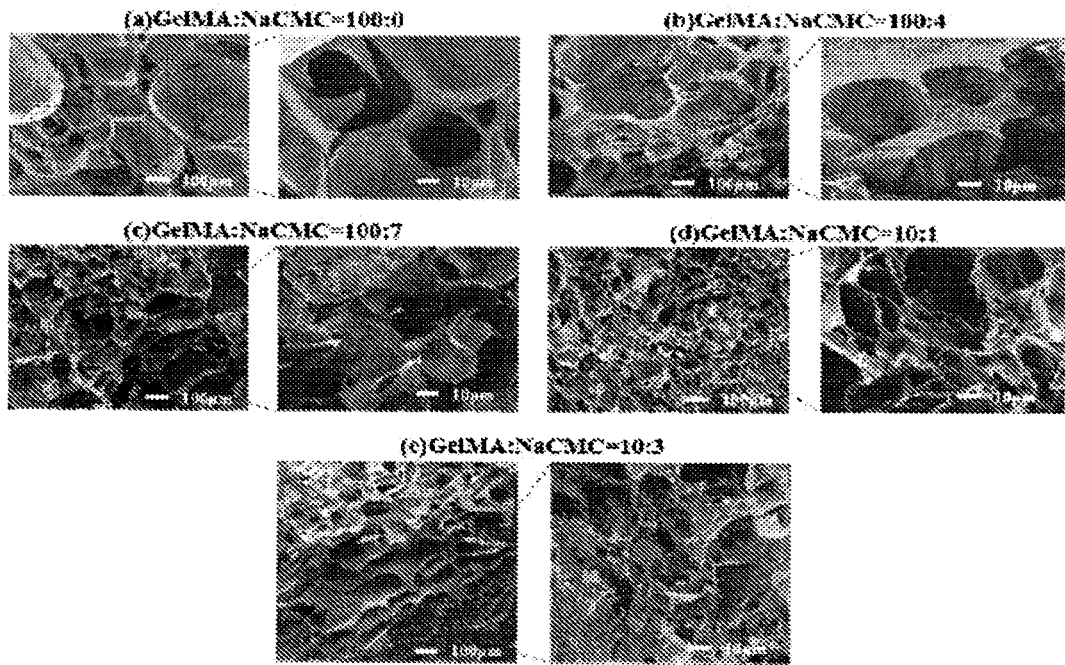
FIG. 2 is a micro-morphology diagram of hydrogel prepared in Examples 1-5 of the present invention under a scanning electron microscope.

Hydrogel microstructure characterization: the hydrogel materials in Example 1, Example 2, Example 3, Example 4 and Example 5 were respectively subjected to curing, freeze drying and metal spraying, and then an internal polymer network of hydrogel was researched through a field emission scanning electron microscope (JEOL, JSM-7610F) under 5 kv alternating current accelerating voltage, as shown in FIG. 2. It can be seen through an electron microscope graph that the interiors of all hydrogel components are of porous structures, and it can be found through comparison that along with increasing of the content of sodium carboxymethyl cellulose, the structural size of internal micropores is reduced, and the pore density is increased. These phenomena show that after the hydrogel of different concentrations is successfully crosslinked, the crosslinking morphology structure of the hydrogel is changed, the higher the concentration is, the greater the influence on the crosslinking structure is, and the denser the structure is.

Figure 3:
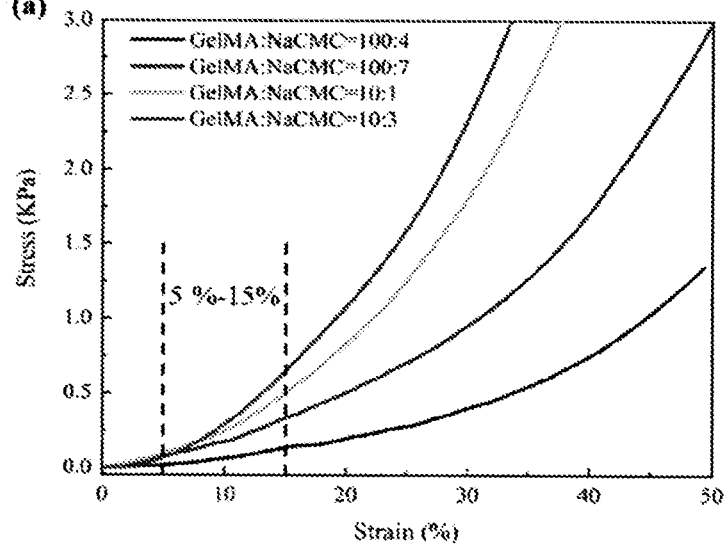
FIG. 3 is a compression modulus diagram of hydrogel prepared in Examples 2-5 of the present invention.
Figure 3:
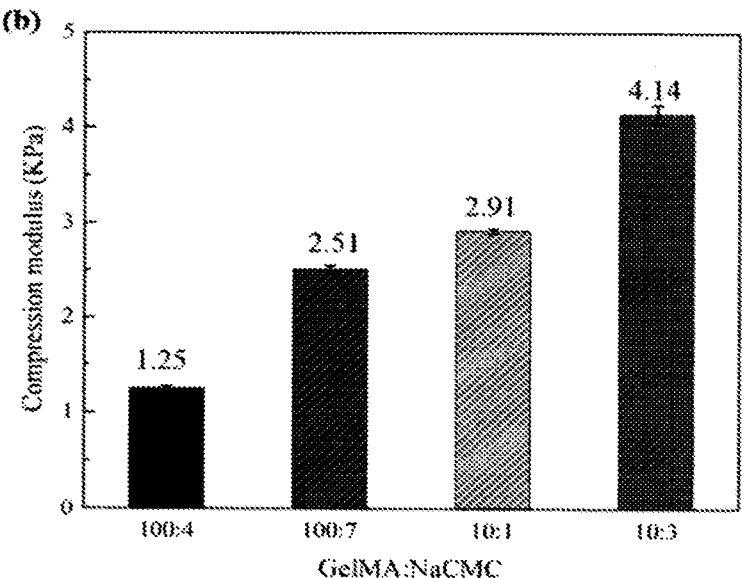

Mechanical performance characterization: the characterization was performed on the mechanical performance of hydrogel in air at a loading rate of 1 mm/min through a universal testing machine (ZLC-2D, Jinan XLC Testing Machine Co., Ltd.) and a 100 n weighing sensor, as shown in FIG. 3. As shown in FIG. 3*a*, the stress changes faster along with strain as the content of NaCMC increases, and the breaking strain value of the hydrogel is smaller. As shown in FIG. 3*b*, the higher the NaCMC content is, the stronger the hydrogel network is, which leads to the enhancement of the mechanical strength, and the larger the compression modulus of the hydrogel is (1.25 KPa under GelMA:NaCMC=100:4, 2.51 KPa under GelMA:NaCMC=100:7, 2.91 KPa under GelMA:NaCMC=10:1, and 4.14 KPa under GelMA:NaCMC=10:3). For soft tissue of an organism such as brain tissue, the soft part (100-500 Pa) is extremely beneficial to neuron growth, and the hard part (1,000-10,000 Pa) is beneficial to promotion of glial cell culture. Therefore, through a compression test, the compression modulus of the obtained hydrogel is smaller than 10 KPa, which indicates that the hydrogel has an application prospect in neuron culture in the field of brain tissue.

Figure 4:
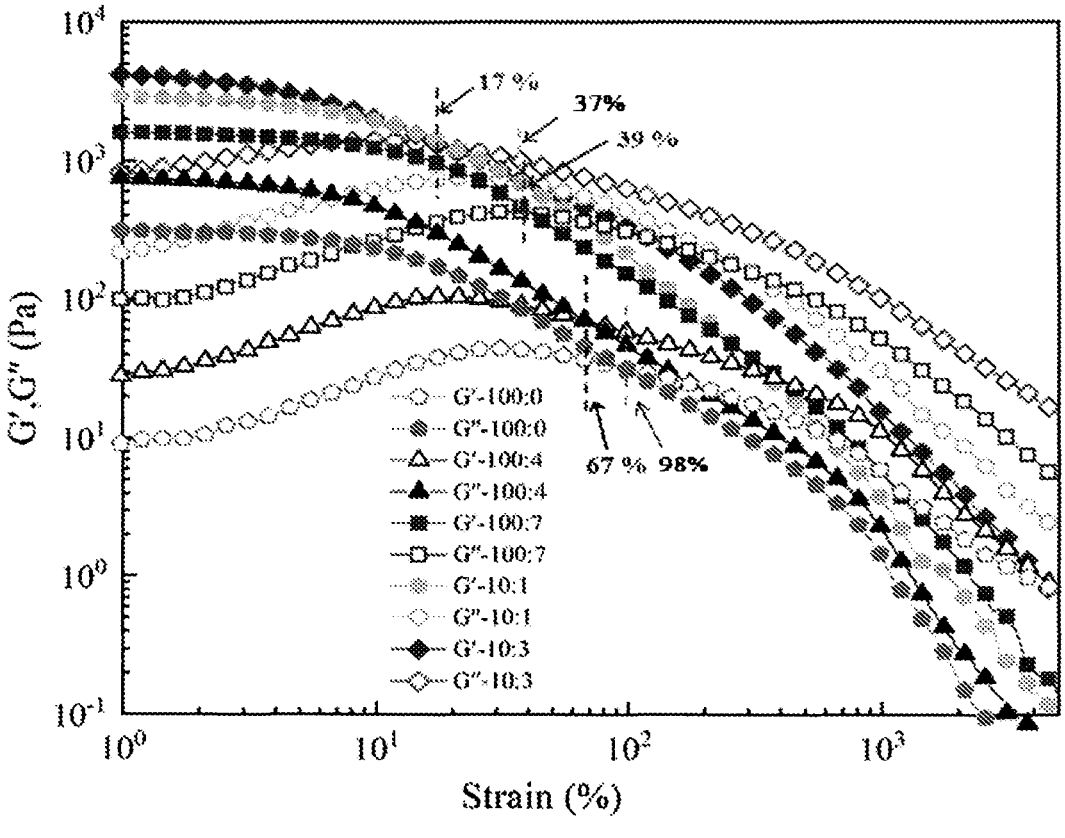
FIG. 4 is a rheological property diagram of hydrogel prepared in Examples 1-5 of the present invention.

Rheological property characterization: rheological analysis was carried out on the hydrogel at room temperature by Anton Paar MCR-302 and a 1° cone plate, as shown in FIG. 4. In the experiment, in order to prevent water loss, silicone oil was adopted to seal the edge of a flat plate. As shown in FIG. 4, the storage modulus G' is continuously reduced along with the increase of strain and gradually approaches to the loss modulus G″, which indicates that the cured hydrogel network starts to break as the strain increases. Then, a storage modulus G' curve is intersected with a loss modulus G' curve at a certain critical strain position to form an intersection point. When the strain is greater than the critical value, G' is smaller than G″, which indicates that the gel converts into fluid from solid due to the collapse of the polymer network. In addition, the larger the mass ratio of GelMA:NaCMC is in the gel, the larger the G' value is before the intersection point is formed, and the smaller the strain value at the intersection point is (98% under GelMA:NaCMC=100:0, 67% under GelMA:NaCMC=100:4, 39% under GelMA:NaCMC=100:7, 37% under GelMA:NaCMC=10:1, and 17% under GelMA:NaCMC=10:3). This indicates that the larger the mass ratio of the gel to NaCMC is, the harder the cured gel is, but the brittleness of the cured gel is much smaller, so the cured gel is easier to break.

Cytotoxicity characterization: the biocompatibility of materials was verified through a cell proliferation experiment, and activity of cells in material leach liquor was evaluated through a CCK-8 reagent. First, L-929 mouse fibroblasts were inoculated into a 96-well plate according to the density of 3,000 cells per well and cultured for 24 h through a complete medium (100 μl/well), and then 4 groups were designed for experiment (a positive control group, a blank control group, a negative control group and an experiment group). The blank control group was continuously cultured through the complete medium, the positive control group was incubated through a 0.65% phenol solution, and the negative control group was incubated through hydrogel leach liquor with the mass ratio of GelMA:NaCMC=100:7. In addition, the experiment group consisted of two types of extracts, one type of extract was a hydrogel extract without NaCMC and CS, and the other type of extract was a hydrogel extract with NaCMC but without CS. The 4 groups were cultured for 1 d, 3 d, 5 d and 7 d at the same time. Working fluid with the volume ratio of 1:10 was prepared through a CCK-8 stock solution and a corresponding medium, and kept away from light for standby application. Detection process: the original medium in the well plate was taken out, then the CCK-8 working fluid was added into the well plate by 110 μl/well, the well plate was placed in an incubator for 2 h, and bubbles should be avoided in the process. Finally, the absorbance of the well plate under the wave length of 450 nm was measured through a multifunctional microplate reader (ReadMax 1900, Shanghai FLASH Spectrum Biotechnology Co., Ltd.), the OD value was read, the number of samples was larger than 5, and the experiment was repeated by n=3. Then, Dixon was used for detecting and eliminating abnormal values, and the data were expressed as the average standard deviation (SD). Finally, the survival ability was expressed by the percentage according to the following equation. Viability=$OD_{450e}/OD_{450b} \times 100\%$ $OD_{450e}$ is the average of the optical density measured in the sample leach liquor; $OD_{450b}$ is the average optical density of the blank group. The lower the survival rate value, the higher the cytotoxic potential of the test sample, and the results are shown in Table 1.

It can be found in the Table 1 that on the 7th d, the cell survival rate of the positive control group in the phenol leach liquor is 25% or below, and the cell grade is 4, which indicates that the sample is toxic. The cell survival rate of the negative control group exceeds 100% from the 5th day, and the cytotoxicity grade is 0, which indicates that the hydrogel sample prepared from the above-mentioned materials is non-toxic to cells. Also, in the experiment group, the cell survival rate of the hydrogel extract without NaCMC and CS exceeds 70% and reaches 75.3% on the 7th day, and the cytotoxicity grade is 1. The cell survival rate of the hydrogel extract with NaCMC but without CS exceeds 80% and reaches 85.4% on the 7th day, and the cytotoxicity grade is 1. Therefore, it indicates that the components added in the hydrogel preparation process do not have cytotoxicity, and the prepared GelMA-based hydrogel promotes cell proliferation to a certain extent and is good in biocompatibility.

TABLE 1

Cytotoxicity test results of hydrogel materials

| Control groups and experiment group | Time (D) | Survival rate (%) | Cytotoxicity grade |
|---|---|---|---|
| Positive control group | 1 | 22.8 | 4 |
| | 3 | 12.6 | 4 |
| | 5 | 6.8 | 4 |
| | 7 | 2.7 | 4 |
| Blank control group | 1 | 100 | 0 |
| | 3 | 100 | 0 |
| | 5 | 100 | 0 |
| | 7 | 100 | 0 |
| Negative control group | 1 | 95.7 | 1 |
| | 3 | 96.7 | 1 |
| | 5 | 100.9 | 0 |
| | 7 | 101.2 | 0 |
| Hydrogel leach liquor without CS | 1 | 81.7 | 1 |
| | 3 | 82.1 | 1 |
| | 5 | 83.7 | 1 |
| | 7 | 85.4 | 1 |
| Hydrogel leach liquor without NaCMC and CS | 1 | 70.2 | 2 |
| | 3 | 71.5 | 2 |
| | 5 | 73.3 | 2 |
| | 7 | 75.3 | 1 |

The foregoing descriptions are merely preferred embodiments of the present invention, but are not intended to limit the present invention. A person skilled in the art may make various alterations and variations to the present invention. Any modification, equivalent replacement, or improvement made within the spirit and principle of the present invention shall fall within the protection scope of the present invention.

What is claimed is:

1. A photocurable composite hydrogel matrix precursor, comprising an aqueous phosphate-buffered saline (PBS) medium and:

(a) 0.25% (w/v) lithium phenyl-2,4,6-trimethylbenzoyl phosphinate (LAP) as a photoinitiator;

(b) 4.2% (w/v) gelatin methacrylate (GelMA);

(c) 0.32% (w/v) sodium alginate;

(d) 0.294% (w/v) sodium carboxymethyl cellulose (NaCMC); and (e) 0.06% (w/v) chondroitin sulfate (CS);

wherein, after ionic crosslinking with an aqueous calcium chloride solution having a mass fraction of 4% for 3 minutes and photocuring using light having a wavelength of 405 nm, a composite hydrogel obtained from the matrix precursor:

(i) has a compressive modulus of less than 10 kPa when measured at a loading rate of 1 mm/min; and (ii) exhibits a cell viability of at least 90% and a cytotoxicity grade of 0 when an extract of the composite hydrogel is used to culture L-929 mouse fibroblasts for 7 days in a CCK-8 assay.

2. A method for preparing the photocurable composite hydrogel matrix precursor according to claim 1, the method comprising:

(1) dissolving the LAP in PBS to form an LAP solution having a concentration of 0.25% (w/v) in PBS;

(2) dissolving GelMA in the LAP solution to form a GelMA solution having a concentration of 10% (w/v), dissolving sodium alginate in the LAP solution to form a sodium alginate solution having a concentration of 2% (w/v), and dissolving NaCMC in the LAP solution to form a NaCMC solution having a concentration of 0.7% (w/v); and (3) mixing 4.2 mL of the GelMA solution, 1.6 mL of the sodium alginate solution, and 4.2 mL of the NaCMC solution to obtain 10 mL of a mixed solution; and (4) adding 0.006 g of chondroitin sulfate into the 10 mL mixed solution and sterile-filtering the resulting solution with a 0.22 μm sterile filter to obtain the composite solution that is the photocurable composite hydrogel matrix precursor.

3. The preparation method according to claim 2, wherein:

in step (1), the LAP solution is photoinitiator continuously heated in a water bath at 60° C. for 30 minutes and oscillated 3 times during heating; and in steps (2)-(3), the dissolving and mixing are performed under continuous heating in a water bath at 60° C. with oscillation performed 3 times during heating.

4. An extrusion-based three-dimensional (3D) bio-printing composite hydrogel scaffold, being prepared by a method comprising:

(1) in a sterile environment, uniformly mixing 1 mL of a photocurable composite hydrogel matrix precursor of claim 1 with $1.0 \times 10^6$ to $1.5 \times 10^6$ mouse fibroblast cells to obtain a cell-laden matrix precursor;

(2) extrusion-printing the cell-laden matrix precursor to form a printed scaffold;

(3) soaking the printed scaffold in an aqueous calcium chloride solution having a mass fraction of 4% for 3 minutes to achieve ionic crosslinking; and (4) photocuring the ionically crosslinked printed scaffold using light having a wavelength of 405 nm to obtain the extrusion-based 3D bio-printing composite hydrogel scaffold.

5. The extrusion-based 3D bio-printing composite hydrogel scaffold according to claim 4, wherein in step (2), the printing speed is 400 mm/min, the moving speed is 900 mm/min, the layer height is 0.25 mm, the number of layers is 3, the distance is 1.5 mm×*1.5 mm, the length×*width is 12 mm×*12 mm, the boundary length is 1 mm, the boundary printing speed is 300 mm/min, the nozzle model is 25 G, the nozzle temperature is 23° C., the receiving platform temperature is 5° C., and the precision air pressure is 27.4 kPa.

* * * * *